United States Patent [19]
Lim

[11] Patent Number: 5,959,557
[45] Date of Patent: Sep. 28, 1999

[54] AUTOCLAVABLE REMOTE HAND CONTROL

[75] Inventor: Joepert R. Lim, Palm Harbor, Fla.

[73] Assignee: Linvatec Corporation, Largo, Fla.

[21] Appl. No.: 08/934,520

[22] Filed: Sep. 22, 1997

[51] Int. Cl.$^6$ .................................................. H03K 17/94
[52] U.S. Cl. .............................. 341/32; 341/23; 341/176; 345/169
[58] Field of Search ............................... 341/23, 32, 176; 345/169; 200/5 R, 5 E

[56] References Cited

U.S. PATENT DOCUMENTS

| | | |
|---|---|---|
| 3,488,613 | 1/1970 | Marchetti . |
| 4,203,013 | 5/1980 | Serras-Paulet . |
| 4,366,463 | 12/1982 | Barker ........................................ 341/32 |
| 4,768,230 | 8/1988 | Viebrantz et al. . |
| 4,791,527 | 12/1988 | Brown . |
| 4,794,489 | 12/1988 | Brown . |
| 4,882,471 | 11/1989 | Kai . |
| 4,916,441 | 4/1990 | Gombrich . |
| 5,092,459 | 3/1992 | Uljanic et al. . |
| 5,175,873 | 12/1992 | Goldenberg et al. . |
| 5,304,209 | 4/1994 | Adams et al. ............................. 607/30 |
| 5,422,783 | 6/1995 | Darbee . |
| 5,422,784 | 6/1995 | Wakahara et al. . |
| 5,443,065 | 8/1995 | Berghoff et al. ......................... 128/639 |
| 5,450,064 | 9/1995 | Williams, Jr. et al. . |
| 5,471,666 | 11/1995 | Sugiyama et al. . |

*Primary Examiner*—Michael Horabik
*Assistant Examiner*—Timothy Edwards, Jr.
*Attorney, Agent, or Firm*—Gene Warzecha

[57] ABSTRACT

An autoclavable remote control unit for controlling the operation of a surgical device. The remote control unit has a plurality of Hall effect sensors arranged on a printed circuit board hermetically encased within a polymeric housing molded from an autoclavable material. Each Hall effect sensor may be activated by an associated magnet which is resiliently supported within a panel which can be closed against the housing or hinged away from the housing. In the closed position, the magnets may be momentarily depressed to activate the associated Hall effect sensor to thereby control the operation of a selected function of the surgical device. The disclosure also includes the method of remotely controlling a surgical device by providing at least one non-contiguously activatable switch element in a hermetically sealed housing and activating the element by bringing into its proximity an activating element.

16 Claims, 4 Drawing Sheets

AUTOCLAVABLE REMOTE HAND CONTROL

BACKGROUND OF THE INVENTION

1. Field of the Invention

The invention relates to surgical control devices. More particularly, the invention relates to surgical control devices which are operatively connected to a main control unit and remotely situated within the surgical arena at some distance from the main control unit.

2. Description of the Prior Art

Remote hand controls have become a necessary accessory for operation of certain surgical devices which are situated within the operating room and must be controlled from the sterile field. An example of such a device is an irrigation pump used during arthroscopic surgical procedures. This pump is an electrically controlled console located in a "non-sterile" environment in the operating room while the patient is located in a "sterile" environment in the operating room. The pump is connected via tubing to the patient but, because of the distance of the pump from the patient, direct operation or control of the pump console is impractical. The pump, being away from the sterile environment where the surgical procedure is being performed, requires a remote control for the surgeon to manually control and adjust pump features and settings. This control should preferably be a small, lightweight remote hand control unit and should not only be able to withstand exposure to disinfectants but should also be autoclavable for sterilization purposes after each use. The autoclavability requirement means the device should be capable of withstanding exposure to approximately 275° F. (121° C.) repeatedly for over 1000 cycles in order to be commercially viable (expecting a minimum of 1600 cycles is not unheard of).

Some prior art surgical remote controls which are not autoclavable can only be used in an operating room if they are enclosed in a transparent plastic bag which may obviate the need for autoclaving the unit after use. This method is cumbersome and clearly not the method of choice and an autoclavable remote would be preferred.

While autoclavable remote hand controls are known and were originally designed to be hermetically sealed and intended to be sterilized using autoclave procedures, success with such remotes has been less than expected because they usually fail after relatively few uses, i.e. autoclave cycles. A common prior art design incorporates an array of domed snap-switches on a printed circuit board encased within a silicone jacket. The thickness of the jacket over the switches is often less than elsewhere on the unit thus sometimes enabling air to permeate the jacket during an autoclave cycle. The expansion and contraction of such "permeated" air and any air trapped within the jacket during manufacture causes such remotes to fail. During the high temperatures of the autoclaving process, the jacket may expand due to its permeability and heating of the residual air within the remote. This air then creates a negative pressure after cooling, sometimes forcing the snap domes to activate or become dislodged. Additionally, some remotes are also large, heavy and bulky in size, thus making them difficult to handle during use. Since surgeons prefer to clamp the remote to a surgical drape, smaller and lighter units are preferable.

Due to the premature failures of the known autoclavable remote hand controls, there is a need for a reliable lightweight surgical remote control that can withstand repeated autoclave cycles.

It is accordingly an object of this invention to produce an autoclavable remote control unit which is reliable over a commercially reasonable number of autoclave cycles.

It is another object of this invention to produce an autoclavable remote control unit which is small, lightweight and easily manipulated by the user with one hand.

It is also an object of this invention to produce an autoclavable remote control unit which is usable without having to be bagged during use.

It is still another object of this invention to produce an autoclavable remote control unit capable of activating a switch element within a hermetically sealed housing by means of non-contiguously activating the switch element from without the housing.

SUMMARY OF THE INVENTION

These and other objects of this invention are achieved by the preferred embodiment disclosed herein which is a remote control handpiece for use with a control means for operating a surgical device comprising a plurality of first switch means arranged in a predetermined pattern and designed for transmitting a predetermined signal to the control means upon activation. A selectively activatable second switch means is juxtaposed relative to each of the first switch means. In the preferred embodiment the first switch means is a Hall effect sensor and the second switch means is a magnet. Movable support means is associated with each of the second switch means and enables selective movement of each of the second switch means relative to the associated first switch means to thereby selectively activate or deactivate the first switch means. A housing hermetically encases the first switch means and enables non-contiguous activation of the first switch means by the second switch means.

The invention also resides in a method of producing activating signals in a remote control handpiece for use with a control means for operating a surgical device comprising the steps of providing a first switch means for controlling, upon activation thereof, an operation in the control means. The method further comprises hermetically encasing the first switch means in an autoclavable housing; providing a second switch means for activating the first switch means; and juxtapositioning the second switch means adjacent the first switch means. The second switch means is normally biased away from the first switch means but it is resiliently supported so it can be moved closer to the first switch means to activate it.

DESCRIPTION OF THE PREFERRED EMBODIMENT

Figure 1:
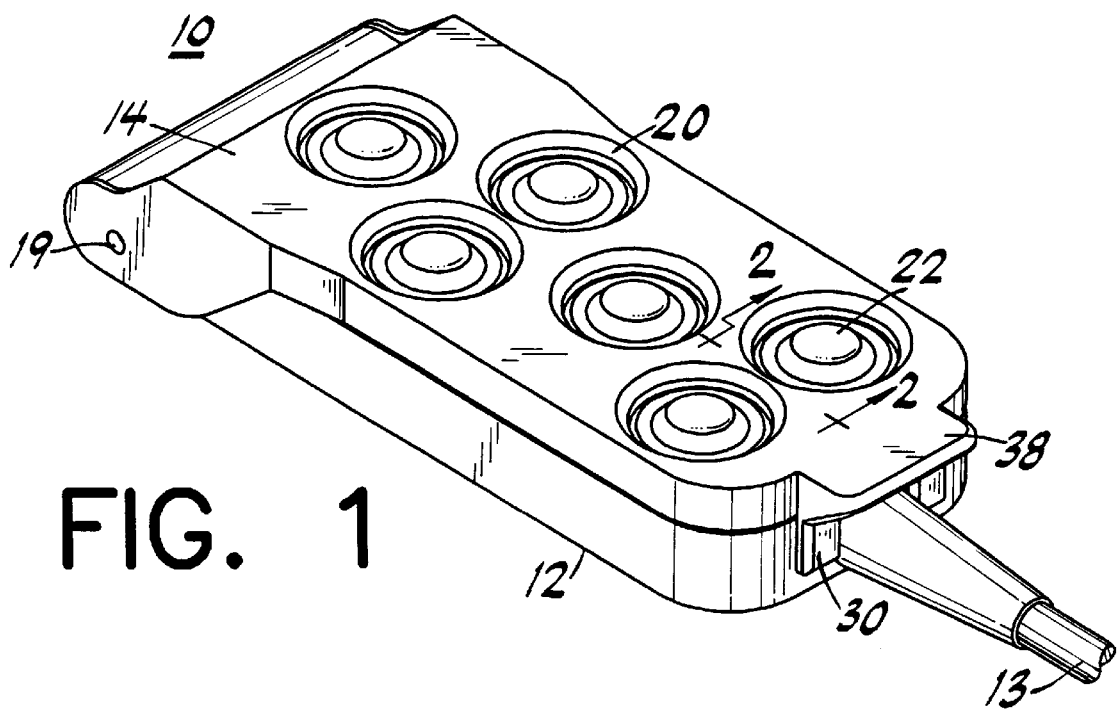
FIG. 1 is a front perspective view of a remote control unit constructed in accordance with the principles of this invention.
Figure 2:
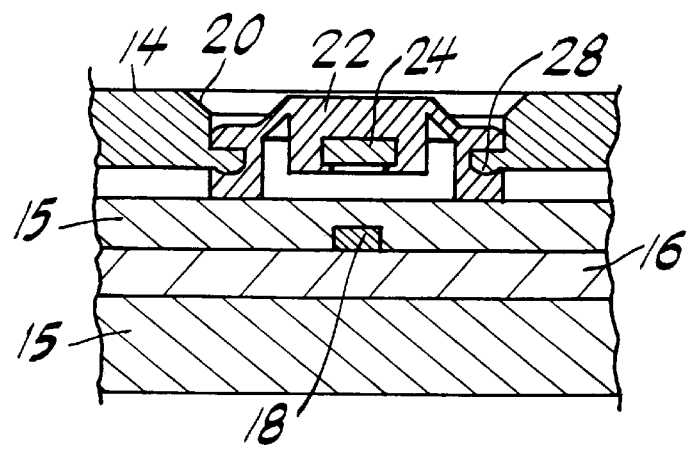
FIG. 2 is a cross-sectional view of FIG. 1 taken along the line 2—2.
Figure 3:
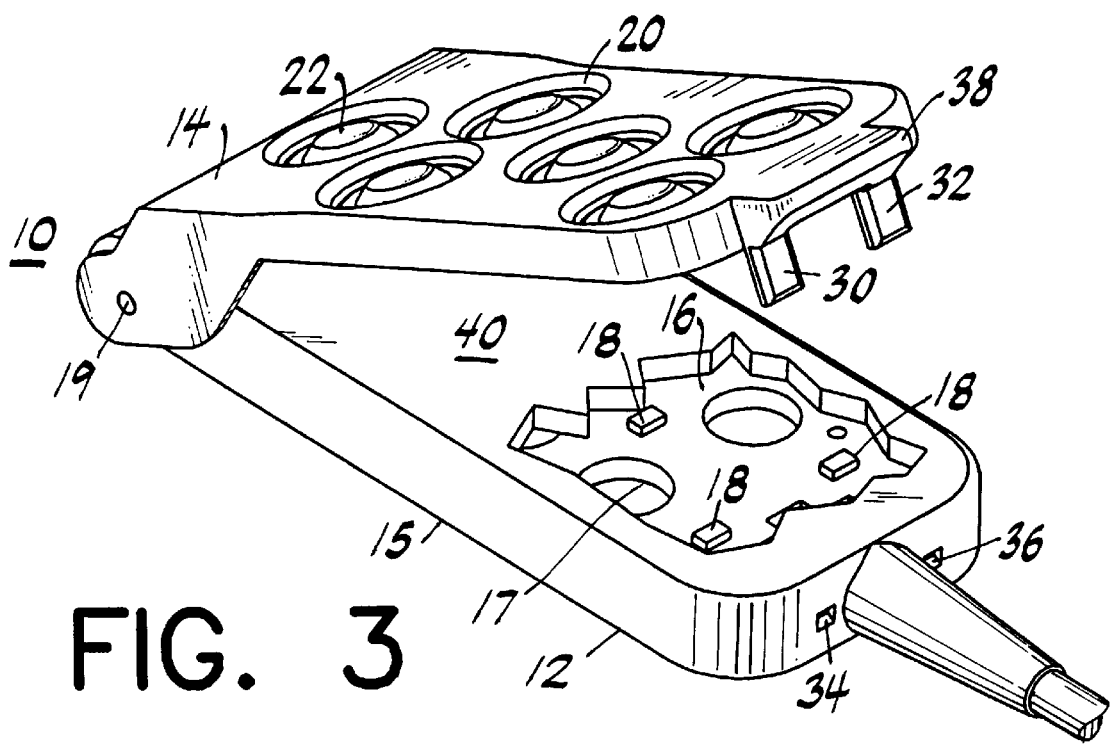
FIG. 3 is a partially cutaway front perspective view of a remote control unit constructed in accordance with the principles of this invention showing two portions thereof spaced from each other.
Figure 6:
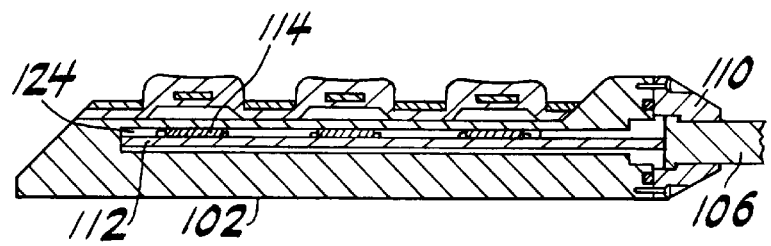
FIG. 6 is a cross-sectional view of the embodiment of FIG. 4 with the two spaced portions of FIG. 4 shown juxtaposed together.
Figure 4:
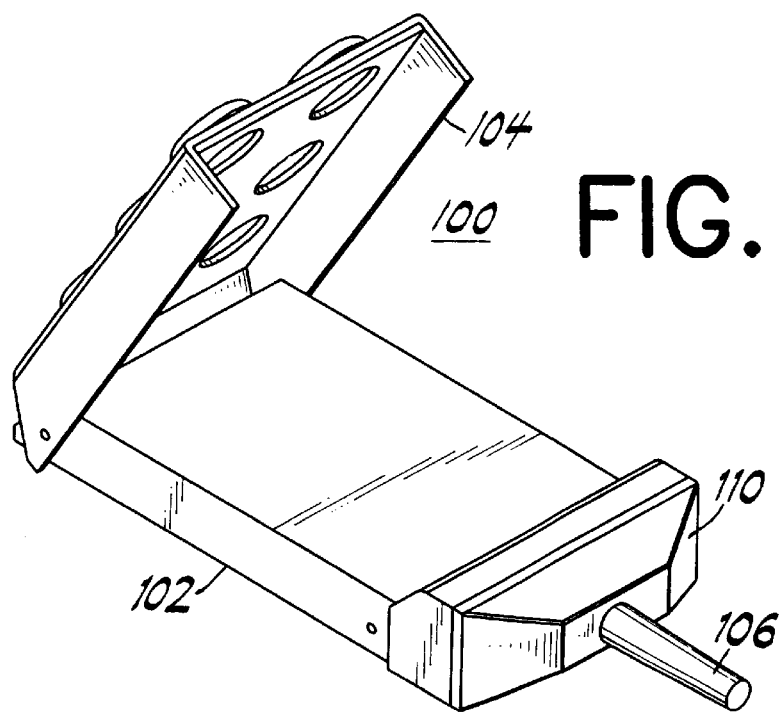
FIG. 4 is a front perspective view of an alternate embodiment of a remote control unit showing two portions thereof spaced from each other.
Figure 5:
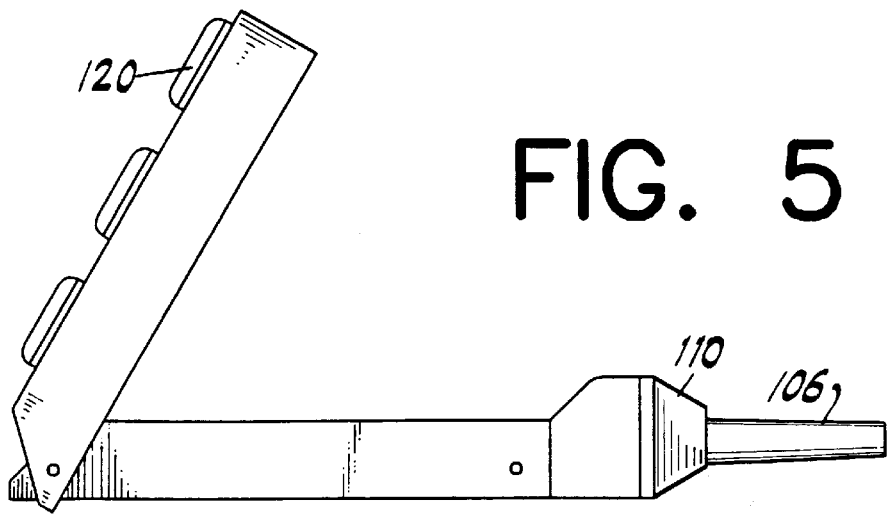
FIG. 5 is a side elevational view of FIG. 4.

As shown in FIGS. 1–3, an autoclavable remote hand control unit 10 comprises a molded base 12, a cable assembly 13 and a button panel 14. The remote hand control 10 makes a plurality of manually operable switches available to a user to remotely control the operation of a main console or surgical device (not shown) to which the other end of the cable may be connected. Base 12 encases within a silicone based molding material 15 a circuit in the form of a printed circuit board 16 carrying a plurality of first switch elements such as Hall effect sensors 18 arranged in a predetermined pattern. Each sensor comprises one part of a switch or circuit element which is non-contiguously activatable by another part which is on panel 14. As used herein, the term "non-contiguous" refers to the activation of a first element by bringing a second element into the proximity of the first element without the first and second elements touching each other. While the preferred embodiment utilizes Hall effect sensors and magnets, the term "switch means" is used herein to encompass other possible arrangements wherein a switch, switch element or other signal transmitting device may be remotely connected to a main console and non-contiguously activated—e.g. opened or closed—by some activating stimulus. (One example of such an alternate embodiment is the magnetic reed switches shown in FIGS. 4–7.)

In the preferred embodiment, panel 14 is hinged to base 12 by a pair of hinge pins 19 (only one shown) and is provided with a plurality of apertures 20 each of which is adapted to support a flexible, elastomeric (e.g. silicone) button 22 carrying a second switch means such as magnet 24. Each magnet 24 is inserted into a recess in the bottom of a respective one of the silicone buttons and is potted or otherwise sealed or secured therein. In the embodiment shown, these buttons resemble grommets having an annular groove 28 and are assembled into the apertures 20 in the button panel 14. Alternatively, all buttons could be formed as part of a single appropriately shaped silicone sheet received within or attached to panel 14. Each button (or, if a single sheet, at least the area around each magnet) is resilient and biased so that with the panel 14 closed (as shown in FIG. 1) and without manual pressure the magnet is spaced sufficiently away from the surface of base 12 (as shown in FIG. 2) to be unable to activate the associated sensor. All magnets 24 are thus arranged in an array which juxtapositions them over corresponding Hall sensors 18 when panel 14 is in a closed, operational position as shown in FIG. 1. Momentary pressure on a selected button will non-contiguously activate the associated Hall sensor by placing the magnet sufficiently close to the sensor. Panel 14 may include a pair of closure tabs 30, 32 releasably engageable with a pair of detents 34, 36 to hold the panel closed. Gripping tab 38 facilitates opening and closing the panel. While panel 14 is shown hingedly attached to base 12, it may be made totally detachable from the base or it may be made fixedly attached in the form of an open grid or cage for holding the buttons spaced from the surface of the base to facilitate cleaning. The resiliency of the buttons provides a positive, tactile feedback to the user so that he or she has some indication that the chosen switch or function has been activated when the button is pushed. Releasing the button allows it to snap back into its normally biased position. Other tactile or audible mechanisms may also be devised within the scope of this invention.

Cable 13 attached to printed circuit board 16 connects the molded base 12 to a control console (for example, an irrigation pump, not shown) by a connector (not shown). The cable contains a plurality of signal conducting wires connecting the printed circuit to the main console. This cable/printed circuit board assembly is insert molded with silicone in order to produce base 12 without trapping any air inside. Apertures 17 in the printed circuit board enables the liquid silicone to bond the board securely. While silicone is used in the preferred embodiment, one may use any elastomeric material suitable for hermetically sealing printed circuit board 16 and its associated elements. Panel 14 is then attached to the cable/printed circuit board assembly thereby aligning the magnets and the Hall sensors for operation.

It will be understood that the invention is usable without a physical connection to the main console. That is, an infrared or other optical or non-optical device could transmit signals to the console without the need for a cable.

Remote control 10 is shown in an operational position in FIG. 1 where panel 14 lies adjacent the upper surface 40 of base 12. This position enables all magnets 24 to overlie their corresponding Hall sensors 18 as best seen in FIG. 2. Simple depression of a selected button 22 moves its magnet 24 closer to its corresponding Hall sensor 18 in order to activate the particular function defined by that sensor. The various functions (in a pump, for example) may include power on/off, flow up/down, pressure up/down, etc. When panel 14 is partially moved away from base 12 as shown in FIG. 3 (or even fully open so that panel 14 lies flat in the same plane as base 12, not shown) the remote control 10 may be easily cleaned and autoclaved without doing anything more complicated than simply unlatching closure tabs 30 and 32 by pulling on tab 38.

Hinged panel 14 is used in the preferred embodiment to enable switch buttons 22 to be separable from the Hall sensors 18. Other such separation means may be suitable as well. This enables switch operation in one position while facilitating cleaning and sterilization in another position. Also, insert molding the printed circuit board assembly and Hall sensors into a silicone base and using Hall sensors eliminates air pockets inside the housing, thus preventing false activation of the switches. A remote control unit constructed in accordance with the foregoing description has passed 1,600 autoclave cycles with no deterioration of either button functionality or materials.

Figure 7:
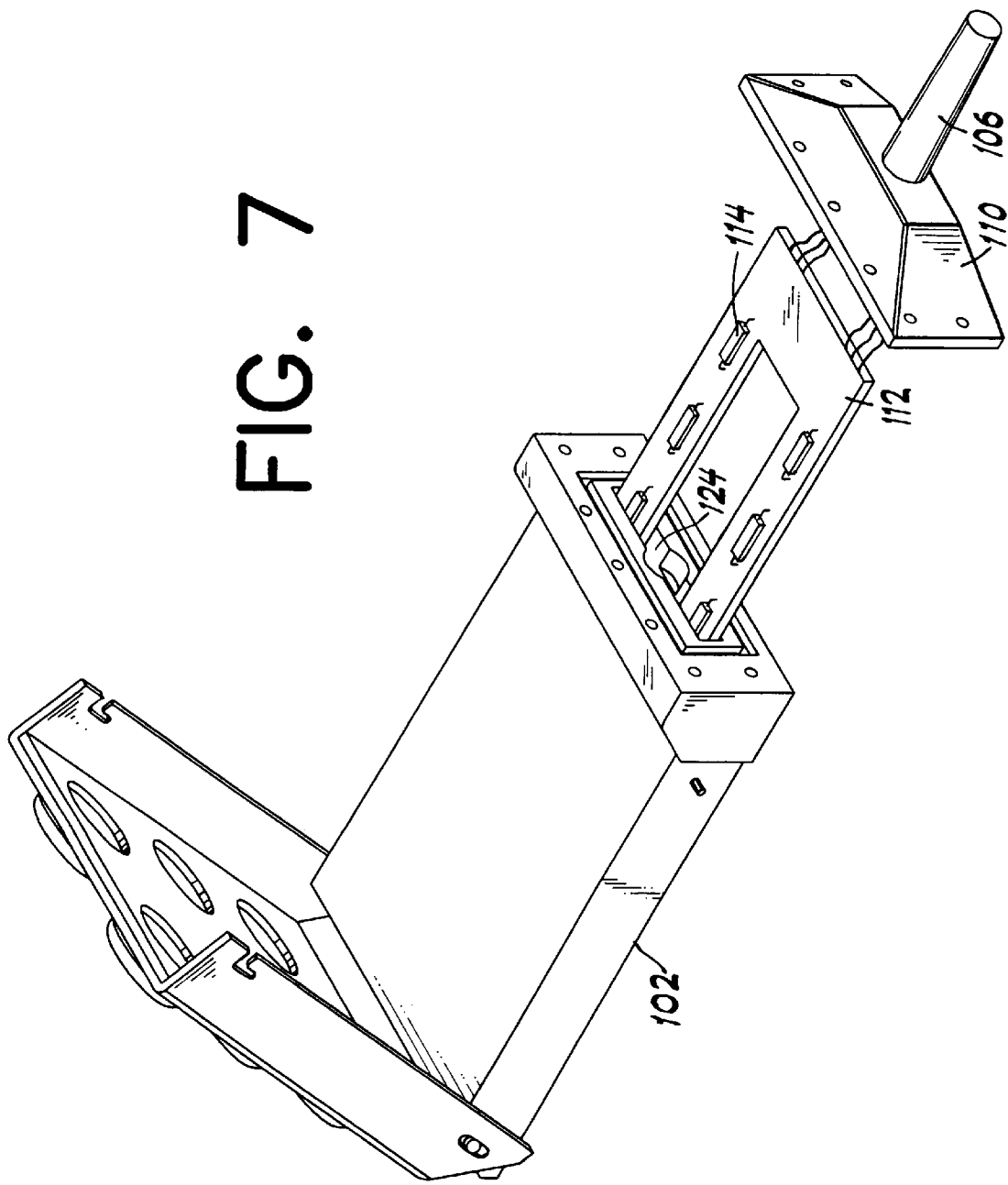
FIG. 7 is an exploded front perspective view of the embodiment of FIG. 4.

An alternative embodiment of the invention is shown in FIGS. 4–7 in which the remote control 100 comprises a base 102 and a hinged panel 104. Cable assembly 106 is attached to an adapter plate 110 which is attachable to base 102. Printed circuit board 112 is operatively connected to cable 106 and carries a plurality of magnetic switch contacts 114 (e.g. reed switches) arranged in a predetermined pattern which, as shown in FIG. 7, may be a simple rectangular array. As with the previous embodiment, panel 104 has a plurality of apertures each of which retains a flexible elastomeric button 120 intended to activate a corresponding magnetic switch 114. In this embodiment, base 102 may be an aluminum, plastic or elastomeric casing having a recess 124 to receive the printed circuit board 112. Suitable seal means between cable plate 110 and base 102 may be used to make the assembly hermetically sealed.

The invention is also embodied in the method of producing an autoclavable remote control. The method comprises the steps of providing a hermetically sealed base having a first array of switch elements, each switch element being non-contiguously responsive to an activating stimulus, and providing a second array of activators for producing the activating stimulus. The method further comprises juxtaposing the first and second arrays in parallel orientation to enable each of the activators to activate a corresponding one of the switches. The method may further comprise the step of hingedly or detachably (fully or partially) attaching the second array to a cover which is movable relative to the base to facilitate the cleaning and sterilization of the remote control.

While the preferred embodiment has been shown in the form of a flat array of switch elements on a remote control unit, it will be understood that other shapes may be produced. The activating stimulus which non-contiguously triggers the hermetically sealed switch means simply needs to be sufficiently movable into proximity to activate the circuit by closing the switch. Non-contiguously activatable elements other than Hall effect sensors or reed switches may also be used. For example, infrared or optical means on the movable panel could be used to trigger a switch means within the sealed base. Other mechanical, electrical, piezoelectrical, hydraulic, fluidic, pneumatic, etc. trigger devices may be devised to non-contiguously trigger a switch element hermetically sealed within an impervious housing by using an element situated outside of the housing.

It will be understood by those skilled in the art that numerous improvements and modifications may be made to the preferred embodiment of the invention disclosed herein without departing from the spirit and scope thereof.

What is claimed is:

1. A remote control handpiece for use with a control means for operating a surgical device comprising:
   a plurality of first switch means arranged in a predetermined pattern, said first switch means for transmitting at least one predetermined signal to said control means upon activation;
   a plurality of selectively activatable second switch means, each one of which is juxtaposed relative to a respective one of said first switch means for activating same;
   movable support means associated with said second switch means for enabling selective movement of each of said second switch means relative to said respective ones of said first switch means to thereby selectively activate or deactivate selected ones of said first switch means; and
   an air-tight housing hermetically encasing said first switch means to thereby enable said handpiece to be autoclaved, said housing enabling non-contiguous activation of said first switch means by said second switch means.

2. A remote control handpiece according to claim 1 wherein said movable support means is resilient.

3. A remote control handpiece according to claim 1 wherein said first switch means comprises Hall effect sensors and said second switch means comprises magnetic elements.

4. A remote control handpiece according to claim 1 wherein a single discrete resilient support means is associated with a single one of said second switch means.

5. A remote control handpiece according to claim 1 further comprising a panel member for holding said support means and wherein said second switch means are arranged in said predetermined pattern on said panel member which may be moved between a first, operable position in which selected ones of said first switch means can be activated by movement of selected ones of said second switch means and a second, inoperable position in which said selected ones of said first switch means cannot be activated.

6. A remote control handpiece according to claim 1 wherein said support means normally biases selected ones of said second switch means away from said first switch means in a deactivating position.

7. A remote control handpiece according to claim 1 further comprising an electrical circuit associated with said first switch means and a hermetically sealed signal conducting cable means for operatively connecting said circuit and said first switch means to said control means.

8. A remote control handpiece according to claim 1 wherein said housing is molded from polymeric material.

9. A remote control handpiece for use with a control means for operating a surgical device comprising:
   a printed circuit board comprising at least one first switch means for controlling, upon activation thereof, a predetermined operation in said control means;
   a selectively movable second switch means for activating said at least one first switch means, said second switch means juxtaposed relative to said first switch means;
   support means associated with said second switch means for enabling selective movement of said second switch means relative to said first switch means to thereby selectively affect a circuit comprising said first switch means;
   holding means for positioning said support means in a predetermined position to juxtapose said second switch means adjacent said first switch means; and
   an air-tight housing hermetically encasing said printed circuit board and said first switch means to thereby enable said handpiece to be autoclaved, said housing enabling said second switch means to non-contiguously activate said first switch means.

10. A remote control handpiece for use with a control means for operating a surgical device comprising:
   at least one non-contiguously activatable switch element means for remotely affecting said control means;
   an air-tight housing hermetically encasing said switch element means to thereby enable said handpiece to be autoclaved; and
   activating means for non-contiguously activating said switch element means.

11. A remote control handpiece according to claim 10 further comprising an electrical circuit associated with said switch element means and encased within said housing.

12. A method of producing activating signals in a remote control handpiece for use with a control means for operating a surgical device comprising the steps of:
   providing a first switch means for controlling, upon activation thereof, an operation in said control means;
   hermetically encasing said first switch means in an autoclavable air-tight housing to thereby enable said handpiece to be autoclaved;
   providing a second switch means for activating said first switch means;
   juxtapositioning said second switch means adjacent said first switch means;
   biasing said second switch means away from said first switch means into a first position wherein said first switch means is not activated thereby; and
   moving said second switch means into a second position relative to said first switch means to activate same.

13. A method according to claim 12 wherein said second switch means non-contiguously activates said first switch means.

14. A method according to claim 12 further comprising the step of:

resiliently supporting said second switch means in juxtaposition adjacent said first switch means.

15. A method of producing activating signals in a remote control handpiece for use with a control means for operating a surgical device comprising the steps of:

providing at least one non-contiguously activatable switch element means for controlling, upon activation thereof, an operation in said control means;

hermetically encasing said at least one switch element means in an autoclavable air-tight housing; and non-contiguously activating said switch element means.

16. A method according to claim 15 further comprising the steps of:

resiliently supporting an activating switch element in juxtaposition adjacent said activatable switch element means;

biasing said activating switch element away from said activatable switch element into a first position wherein said activatable switch element means is not activated; and moving said activating switch element into a second position relative to said activatable switch element means to activate same.

* * * * *